United States Patent
Noyori

Patent Number: 6,022,822
Date of Patent: Feb. 8, 2000

[54] ORGANOTIN COMPOUND AND CATALYST FOR TRANSESTERIFICATION COMPRISING THE SAME

[75] Inventor: Ryoji Noyori, Nisshin, Japan

[73] Assignees: Ryoji Noyori, Nisshin; Dainippon Ink and Chemicals, Inc., Tokyo; Sumitomo Company, Ltd., Osaka, all of Japan

[21] Appl. No.: 09/243,413

[22] Filed: Feb. 3, 1999

[30] Foreign Application Priority Data

Feb. 4, 1998 [JP] Japan .................................. 10-022444

[51] Int. Cl.[7] .............................. B01J 31/00; B01J 31/18
[52] U.S. Cl. ...................... 502/152; 502/155; 502/162; 502/167; 502/168; 502/171; 556/81; 556/87; 556/88; 556/89
[58] Field of Search .................................. 502/152, 155, 502/162, 167, 168, 171; 556/81, 87, 88, 89

[56] References Cited

PUBLICATIONS

CA 128:248626, No Month, 1998.
CA 90:104123, No Month, 1978.
CA 89:180111, No Month, 1978.
CA 86:121463, No Month, 1976.

*Primary Examiner*—Elizabeth D. Wood
*Attorney, Agent, or Firm*—Armstrong, Westerman, Hattori, McLeland & Naughton

[57] ABSTRACT

The present invention provides a catalyst for transesterification comprising an organotin compound expressed by the following general formula (I):

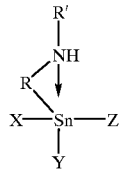

(I)

wherein, X, Y, and Z represent, respectively and independently, an alkoxyl group, alkylthio group, halogen atom, or alkyl group; where at least two groups among X, Y, and Z represent an alkoxyl group, alkylthio group, or halogen atom; R represents an organic chain; and R' represents a hydrogen atom, or alkyl group.

17 Claims, No Drawings

ORGANOTIN COMPOUND AND CATALYST FOR TRANSESTERIFICATION COMPRISING THE SAME

BACKGROUND OF THE INVENTION

1. Field of the Invention

The present invention relates to a novel organotin compound; which can work as a catalyst for transesterification. More specifically, the present invention relates to a catalyst for transesterification which enables for the highly efficient preparation of an ester compound in a high purity under less restrictive conditions.

2. Background Art

Hitherto, organic compounds such as dialkyltin oxide, dialkyltin dicarboxylate, and hydroxymonoalkyltin oxide are widely utilized as effective catalysts for transesterification. For example, preparation of perfluoroalkyl methacrylate by means of transesterification of perfluoroalcohol and methyl methacrylate is disclosed in U.S. Pat. No. 4,360,670, and formation of aromatic dicarboxylic acid diphenyl ester from aromatic dicarboxylic acid and phenyl acetate is described in JP-A-58-213734. An organotin compound could also work as a catalyst in providing diphenyl carbonate from dimethyl carbonate and phenol disclosed in JP-A-8-188558.

However, these organotin compounds described above have low activity for transesterification, and hence, the use of those compounds and the strict reaction conditions, e.g., high reaction temperature, are required in order to achieve a high conversion. In addition, their optical activity is easily lost in the transesterification using a substrate bearing an optically active group. Namely, conventional organotin compounds do not impart a sufficiently high catalytic activity, and many problems have arose in performing reactions with optically active substrates using these catalysts.

SUMMARY OF THE INVENTION

In order to solve the aforementioned problems, it is an object of the present invention (1) to provide an organotin compound catalyst for transesterification that promotes the aforementioned reaction under less restrictive reaction conditions to afford a final product with a high purity and yield, which also does not adversely affect the optical purity; and (2) to provide a method for the preparation of an ester compound in which the aforementioned reaction proceeds simply under less restrictive reaction conditions, while maintaining a high efficiency and the purity of the optical activity.

In order to achieve the aforementioned object, the present invention provides (i) a catalyst for transesterification comprising an organotin compound, expressed by the following general formula (I):

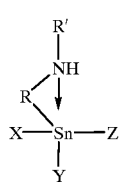

(I)

wherein, X, Y, and Z represent, respectively and independently, an alkoxyl group, alkylthio group, halogen atom, or alkyl group; where at least two groups among X, Y, and Z represent an alkoxyl group, alkylthio group, or halogen atom; R represents an organic chain; and R' represents a hydrogen atom, or alkyl group.

Additionally, in order to achieve the aforementioned object, the present invention provides (ii) a method for preparation of an ester compound by means of transesterification from organic ester compound with an alcohol in the presence of the organotin compound expressed by the above general formula (I) as a catalyst.

Furthermore, in order to achieve the aforementioned object, the present invention provides (iii) an organotin compound expressed by the following general formula (II):

(II)

wherein, X, Y, and Z represent, respectively and independently, an alkoxyl group, alkylthio group, halogen atom, or alkyl group; where at least two groups among X, Y, and Z represent an alkoxyl group, alkylthio group, or halogen atom; R represents an alkylene chain having 3 or 4 carbon atoms, which may contain a substituent group, or in which consecutive carbon atoms may form a part of the ring; and R' represents a hydrogen atom, or alkyl group.

PREFERRED EMBODIMENTS OF THE INVENTION

In the organotin compound expressed by the general formula (I) in the present invention, X, Y, and Z are selected from the group consisting of an alkoxyl group, alkylthio group, and alkyl group; however, a compound in which X, Y, and Z each respectively represents an alkoxyl group is preferred. In addition, R is an organic chain, examples of which may include an alkylene chain; an alkylene chain containing a substituent group; an alkylene chain in which consecutive carbon atoms form a part of a ring such as a saturated hydrocarbon ring, aromatic ring, and heterocyclic ring; and an alkylene chain in which carbon atoms are substituted with bivalent bond groups such as an oxygen atom, sulfur atom, ester bond, and/or amide bond. Any number of atoms between the tin atom and the amino group in the organic chain can be accepted as long as the amino group can coordinate to the tin atom. Among these organic chains, particularly preferred examples include alkylene chain having 3 or 4 carbon atoms, and an alkylene chain in which consecutive carbon atoms form a part of an aromatic ring. In addition, R' represents a hydrogen atom or alkyl group; however, for alkyl group: R', a lower alkyl group having 1~3 carbon atoms is preferred.

The organotin compound expressed by the general formula (I) in the present invention can be prepared, for example, according to the following methods.

(A) Synthesis of an organotin compound: XYZ—Sn—R—NHR' in which X, Y, and Z each respectively represents an alkoxyl group (A-1) In the case of R represented as an alkylene chain First, tricyclohexyltin chloride was synthesized from tin (IV) chloride and tetracyclohexyltin prepared by means of transmetallation of cyclohexyl magnesium bromide and tin(IV) chloride.

Then, a dilithio compound, prepared from an alkanol having a halogen atom with an organolithium compound, is treated with the tricyclohexyltin chloride, to afford hydroxyalkyl (tricyclohexyl)tin. Subsequently, the hydroxyalkyl (tricyclohexyl)tin is reacted with sodium azide leading to a azidoalkyl(tricyclohexyl)tin, followed by reduction to synthesize aminoalkyl (tricyclohexyl)tin.

Further, the aminoalkyl(tricyclohexyl)tin is reacted with tin(IV) chloride, to yield aminoalkyltin trihalide, which is then treated with sodium alkoxide, to obtain the final product of aminoalkyltin trialkoxide.

Examples of the alkanol containing a halogen atom, which is one of the materials for the synthesis, are: primary alkanols such as 3-bromopropanol, 3-bromobutanol, 4-bromobutanol, 3-bromopentanol, 4-bromopentanol, 3-chloropropanol, 3-chlorobutanol, 4-chlorobutanol, 3-chloropentanol, 4-chloropentanol, and the like; secondary alkanols such as 1-methyl-3-bromopropanol, 1-methyl-3-bromobutanol, 1-methyl-4-bromobutanol, 1-methyl-3-bromopentanol, 1-methyl-3-chloropropanol, 1-methyl-3-chlorobutanol, 1-methyl-4-chlorobutanol, 1-methyl-3-chloropentanol, and the like; tertiary alkanols such as 1,1-dimethyl-3-bromopropanol, 1,1-dimethyl-3-bromobutanol, 1,1-dimethyl-4-bromobutanol, 1,1-dimethyl-3-bromopentanol, 1,1-dimethyl-3-chloropropanol, 1,1-dimethyl-3-chlorobutanol, 1,1-dimethyl-4-chlorobutanol, 1,1-dimethyl-3-chloropentanol, and the like.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

If the alkanol possess not only a halogen atom but also other substituent groups, there are such alkanols containing alkyl group as a side chain, for example, 3-bromo-1-methylpropanol, 3-bromo-2-ethylpropanol, 3-chloro-1-ethylpropanol, 3-chloro-2-methylpropanol and the like; alkanols containing a phenyl group as a side chain, for example, 3-bromo-1-phenylpropanol, 3-bromo-2-phenylpropanol, 3-bromo-3-phenylpropanol, 3-chloro-1-phenylpropanol, 3-chloro-2-phenylpropanol, 3-chloro-3-phenylpropanol and the like.

Examples of the alkanol compound containing a halogen atom, possessing a structure in which a portion of the carbon atoms are substituted with bivalent groups such as an oxygen atom and a sulfur atom, are: bromomethyloxymethanol, chloromethyloxymethanol, bromomethylthiomethanol, chloromethylthiomethanol, and the like can be used.

(A-2) In the case of R represented by an alkylene chain in which consecutive carbon atoms form a part of a benzene ring The final product of 2-(aminoalkyl)phenyltin trialkoxide is synthesized in the same manner as the case of A-1, with the use of 2-bromo-1-(hydroxyalkyl)benzene instead of an alkanol containing a halogen atom.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

Examples of the various cyclic compounds containing both a halogen atom and hydroxyalkyl group are: a saturated hydrocarbon cyclic compound such as 1-bromo-2-(2-hydroxyethyl)cyclohexane, and 1-chloro-2-(2-hydroxyethyl)cyclohexane; an aromatic fused cyclic compound containing both a halogen atom and hydroxyalkyl group such as 1-bromo-2-(2-hydroxyethyl)naphthalene, 2-bromo-1-(2-hydroxyethyl)naphthalene, 1-chloro-2-(2-hydroxyethyl)naphthalene, 2-chloro-1-(2-hydroxyethyl) naphthalene, 2-bromo-3-(2-hydroxyethyl)naphthalene, and 2-chloro-3-(2-hydroxyethyl)naphthalene; heterocyclic compound containing both a halogen atom and hydroxyalkyl group such as 2-bromo-3-(2-hydroxyethyl)furan, 3-bromo-3-(2-hydroxyethyl)furan, 2-chloro-3-(2-hydroxyethyl)furan, 3-chloro-3-(2-hydroxyethyl)furan, 2-bromo-3-(2-hydroxyethyl)thiophene, 3-bromo-3-(2-hydroxyethyl) thiophene, 2-chloro-3-(2-hydroxyethyl)thiophene, 3-chloro-3-(2-hydroxyethyl)thiophene, and the like can be used.

(B) Synthesis of an organotin compound: XYZ—Sn—R—NHR' in which X, Y, and Z each respectively represents a halogen atom (B-1) In the case of R represented by an alkylene chain Aminoalkyltin trihalide, which is a synthetic intermediate of the case of A-1, also can be used as a catalyst. In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom are substituted with bivalent group such as an oxygen and sulfur atom, can be used leading to the organotin compounds bearing the corresponding alkylene group R. (B-2) In the case of R represented by an alkylene chain, in which consecutive carbon atoms form a part of a benzene ring In this case, (2-aminoalkylphenyl)tin trihalide, which is a synthetic intermediate in the aforementioned A-2, is used.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.
(C) Synthesis of an organotin compound: XYZ—Sn—R—NHR', in which X, Y, and Z each respectively represents an alkylthio group (C-1) In the case of R represented by an alkylene chain Aminoalkyltin tris(alkylthiolate) is synthesized in the same manner as in the case of A-1, with the sodium thioalkoxide instead of sodium alkoxide.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom are substituted with bivalent group such as an oxygen and sulfur atom, can be used leading to the organotin compounds bearing the corresponding alkylene group R.

(C-2) In the case of R represented by an alkylene chain, which consecutive carbon atoms form a part of a benzene ring 2-aminoalkylphenyltin tris(alkylthiolate) is synthesized in the same manner as in the case of A-1, with the use of 2-bromo-1-(hydroxyalkyl)benzene and sodium thioalkoxide instead of an alkanol containing a bromine atom and sodium alkoxide.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(D) Synthesis of an organotin compound: XYZ—Sn—R—NHR', in which X represents an alkyl group; and Y and Z each respectively represents an alkoxyl group (D-1) In the case of R represented by an alkylene chain After the reaction of aminoalkyltin trichloride, obtained in the case of B-1, with two equivalent of sodium alkoxide, the remaining halogen atom is further reacted with an alkyl lithium, to afford the final product of alkyl(aminoalkyl)tin dialkoxide.

Examples of the alkyl lithium are: methyl lithium, ethyl lithium, n-propyl lithium, n-butyl lithium, and the like.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

(D-2) In the case of R represented by an alkylene chain, in which consecutive carbon atoms form a part of a benzene ring After the reaction of 2-aminoalkylphenyltin trihalide, obtained in the case of B-2, with two equivalent of sodium alkoxide, the remaining halogen atom is further reacted with an alkyl lithium, to afford the final product of alkyl(2-aminoalkylphenyl)tin dialkoxide.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(E) Synthesis of an organotin compound: XYZ—Sn—R—NHR' in which X represents an alkyl group; and Y and Z each respectively represents a halogen atom (E-1) In the case of R represented by an alkylene chain Aminoalkyltin trihalide obtained in the case of B-1, is reacted with an equivalent of an alkyl lithium, to synthesize the final product of dihalogenomonoalkylaminoalkyltin.

In the same manner according to invention, it is also possible to synthesize an organotin compound in which R is alkylen chain having a substituent group by means of using alkanol containing not only a halogen atom and but also other substituent group.

As another alkanol containing a halogen atom, the alkanol, in which a portion of the carbon atom are substituted with bivalent group such as an oxygen and sulfur atom, can be used leading to the organotin compounds bearing the corresponding alkylene group R.

(E-2) In the case of R represented by an alkylene chain, which consecutive carbon atoms form a part of a benzene ring 2-(aminoalkyl)phenyl)tin trihalide obtained in the case of B-2, is reacted with an equivalent of an alkyl lithium, to synthesize the final product of dihalogenomonoalkyl (2-aminoalkyl)phenyl)tin.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(F) Synthesis of an organotin compound: XYZ—Sn—R—NHR' in which X represents an alkyl group; and Y and Z each respectively represents an alkylthio group (F-1) In the case of R represented by an alkylene group After the reaction of aminoalkyltin trihalide, obtained in the case of B-1, with two equivalent of sodium thioalkoxide, the reactant is further treated with an equivalent of an alkyl lithium, to afford the final product of alkyl(aminoalkyl)tin bis(alkylthiolate).

In the same manner according to invention, it is also possible to synthesize an organotin compound in which R is alkylen chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

(F-2) In the case of R represented by an alkylene chain, which consecutive carbon atoms form a part of a benzene ring After the reaction of 2-(aminoalkyl)phenyltin trihalide, obtained in the case of B-2, with two equivalent of sodium thioalkoxide, the reactant is further treated with an equivalent of an alkyl lithium, to afford the final product of alkyl(2-aminoalkyl)phenyltin bis(alkylthiolate).

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(G) Synthesis of an organotin compound: XYZ—Sn—R—NHR' in which X represents an alkyl group; Y represents an alkoxyl group; and Z represents a halogen atom (G-1) In the case of R represented by an alkylene group After the reaction of aminoalkyltin trichloride, obtained in the case of B-1, with an equivalent of sodium alkoxide, the reactant is further treated with an equivalent of an alkyl lithium, to afford the final product of alkyl(alkoxyl) (aminoalkyl)tin monohalide.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

(G-2) In the case of R represented by an alkylene chain, which consecutive carbon atoms form a part of a benzene ring After the reaction of 2-(aminoalkyl)phenyltin trihalide, obtained in the case of B-2, with an equivalent of sodium alkoxide, the reactant is further treated with an equivalent of an alkyl lithium, to afford the final product of alkoxy(alkyl)(2-aminoalkyl)phenyltin monohalide.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(H) Synthesis of an organotin compound: XYZ—Sn—R—NHR' in which X represents an alkyl group; Y represents an alkoxyl group; and Z represents an alkylthio group (H-1) In the case of R represented by an alkylene chain After the reaction of aminoalkyltin trihalide, obtained in the case of B-1, with an equivalent of sodium alkoxide, the reactant is further treated with an equivalent of sodium thioalkoxide, followed by the reaction with an equivalent of an alkyl lithium, to afford the final product of alkoxy(alkyl)(aminoalkyl)tin monoalkylthiolate.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

(H-2) In the case of R represented by an alkylene chain, in which consecutive carbon atoms form a part of a benzene ring After the reaction of 2-(aminoalkyl)phenyltin trihalide, obtained in the case of B-2, with an equivalent of sodium alkoxide, the reactant is further treated with an equivalent of sodium thioalkoxide, followed by the reaction with an equivalent of an alkyl lithium, to afford the final product of alkoxy(alkyl)(2-aminoalkyl)phenyltin monoalkylthiolate.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(J) Synthesis of an organotin compound: XYZ—Sn—R—NHR' in which X represents an alkyl group; Y represents a halogen atom; and Z represents an alkylthio group (J-1) In the case of R represented by an alkylene chain After the reaction of aminoalkyltin trichloride, obtained in the case of B-1, with an equivalent of sodium thioalkoxide, the reactant is further treated with an equivalent of an alkyl lithium, to afford the final product of alkyl(alkylthio)(aminoalkyl)tin monohalide.

In the same manner according to invention, it is also possible to synthesize an organotin compound in which R is an alkylene chain having a substituent group by means of using alkanol containing not only a halogen atom and but also other substituent group.

As another alkanol containing a halogen atom, the alkanol, in which a portion of the carbon atom is substituted with bivalent group such as an oxygen and sulfur atom, can be used leading to the organotin compounds bearing the corresponding alkylene group R.

(J-2) In the case of R represented by an alkylene chain, which consecutive carbon atoms form a part of a benzene ring After the reaction of 2-(aminoalkyl)phenyltin trihalide, obtained in the case of B-2, with an equivalent of sodium thioalkoxide, the reactant is further treated with an equivalent of alkyl lithium, to afford the final product of alky(alkylthio)(2-(aminoalkyl)phenyl)tin monohalide.

According to invention, it is also possible to use other various cyclic compounds, such as a saturated hydrocarbon ring, aromatic ring, and heterocycles, containing both a bromine atom and hydroxyalkyl group heading to the organotin compounds.

In the final product, alkylene chain R can be regarded as to have two substituent groups which form ring structure.

(K) Synthesis of an organotin compound: XYZ—Sn—R—NHR' in which R represents an alkylene chain It is also possible to prepare a compound in which R represents an alkylene chain, particularly a propylene chain, according to the following method.

That is, after the reaction of trialkyltin hydride with an acrylonitrile derivative in the presence of a polymerization initiator, 3-trialkylstannylpropylamine derivative is prepared from the reduction of nitrile groups to amino groups by lithium aluminum hydride or the like. Subsequently, the 3-trialkylstannylpropylamine derivative is treated with tin tetrachloride, to afford tin(IV) trichloride derivative, which is further reacted with sodium alkoxide, to yield the final product of 3-aminopropyltin[tri(alkoxide)].

Examples of the trialkyltin hydride, employed in this synthesis method, may include trimethyltin hydride, triethyltin hydride, tri n-propyltin hydride, tri i-propyltin hydride, and the like.

Additionally, in this synthesis method, it is possible to use tricyclopentyltin hydride, tricyclohexyltin hydride, triphenyltin hydride, and the like, instead of trialkyltin hydride.

Examples of the acrylonitrile derivative, employed in this synthesis method, may include an acrylonitrile, methacrylonitrile, 2-propionitrile, and the like.

Examples of the polymerization initiator, employed in the reaction of trialkyltin hydride with acrylonitrile derivative, may include any compound generally used as an initiator in a radical reaction; however, concrete examples may include an azobisisobutyronitrile, azobis-t-butoxyl, benzoyl peroxide, t-butyl peroxide, t-butylhydro peroxide, and the like.

The method for synthesizing the aforementioned 3-aminopropyltin [tri(alkoxide)] can also be applied correspondingly for the synthesis of other compounds expressed by the general formula (I), wherein R represents a propylene chain. That is, a compound, expressed by the general formula (I), wherein X, Y, and Z each respectively represents a halogen atom or alkylthio group; a compound, expressed by the general formula (I), wherein X represents an alkyl group, Y and Z each respectively represents an alkoxyl group or halogen atom; and a compound, expressed by the general formula (I), wherein X represents an alkyl group, Y represents an alkoxyl group, and Z represents a halogen atom or alkylthio group.

Concrete examples of the organotin compound (A), expressed by the general formula (I), wherein X, Y, and Z each respectively represents an alkoxyl group are: o-(1-aminoethyl)phenyltin trimethoxide, o-(1-aminoethyl)phenyltin triethoxide, o-(1-aminoethyl)phenyltin tri(n-propoxide), o-(1-aminoethyl)phenyltin tri(i-propoxide), o-(1-aminoethyl)phenyltin tri(n-butoxide), o-(1-aminoethyl)phenyltin tri(i-butoxide), o-(1-aminoethyl)phenyltin tri(sec-butoxide), o-(aminomethyl)phenyltin trimethoxide, o-(aminomethyl)phenyltin triethoxide, o-(aminomethyl)phenyltin tri(n-propoxide), o-(aminomethyl)phenyltin tri(i- propoxide), o-(1-aminomethyl)phenyltin tri(n-butoxide), o-(aminomethyl)phenyltin tri(i-butoxide), o-(aminomethyl) phenyltin tri(sec-butoxide), 3-aminopropyltin trimethoxide, 3-aminopropyltin triethoxide, 3-aminopropyltin tri(n-propoxide), 3-aminopropyltin tri(i-propoxide), 3-aminopropyltin tri(n-butoxide), 3-aminopropyltin tri(i-butoxide), 3-aminopropyltin tri(sec-butoxide), 2-ethylaminoethyltin trimethoxide, 2-ethylaminoethyltin triethoxide, 2-ethylaminoethyltin tri(n-propoxide), 2-ethylaminoethyltin tri(i-propoxide), 2-ethylaminoethyltin tri(n-butoxide), 2-ethylaminoethyltin tri(i-butoxide), 2-ethylaminoethyltin tri(sec-butoxide), 2-methylaminoethyltin trimethoxide, 2-methylaminoethyltin triethoxide, 2-methylaminoethyltin tri(n-propoxide), 2-methylaminoethyltin tri(i-propoxide), 2-methylaminoethyltin tri(n-butoxide), 2-methylaminoethyltin tri(i-butoxide), 2-methylaminoethyltin tri(sec-butoxide), 3-ethylaminopropyltin trimethoxide, 3-ethylaminopropyltin triethoxide, 3-ethylaminopropyltin tri(n-propoxide), 3-ethylaminopropyltin tri(i-propoxide), 3-ethylaminopropyltin tri(n-butoxide), 3-ethylaminopropyltin tri(i-butoxide), 3-ethylaminopropyltin tri(sec-butoxide), 3-methylaminopropyltin trimethoxide, 3-methylaminopropyltin triethoxide, 3-methylaminopropyltin tri(n-propoxide), 3-methylaminopropyltin tri(i-propoxide), 3-methylaminopropyltin tri(n-butoxide), 3-methylaminopropyltin tri(i-butoxide), 3-methylaminopropyltin tri(sec-butoxide), 4-ethylaminobutyltin trimethoxide, 4-ethylaminobutyltin triethoxide, 4-ethylaminobutyltin tri(n-propoxide), 4-ethylaminobutyltin tri(i-propoxide), 4-ethylaminobutyltin tri(n-butoxide), 4-ethylaminobutyltin tri(i-butoxide), 4-ethylaminobutyltin tri(sec-butoxide), 4-methylaminobutyltin trimethoxide, 4-methylaminobutyltin triethoxide, 4-methylaminobutyltin tri(n -propoxide), 4-methylaminobutyltin tri(i-propoxide), 4-m ethylaminobutyltin tri(n-butoxide), 4-methylaminobutyltin tri(i-butoxide), 4-methylaminobutytin tri(sec-butoxide), 2-(1-aminoethyl)cyclohexyltin triethoxide, 2-(4-aminoethyl)naphthalene-3-yltin triethoxide, 2-(1-aminoethyl)furan-3-yltin triethoxide, 2-(1-aminoethyl)thiophene-3-yltin triethoxide, 3-ethylamino-2-methylpropyltin triethoxide, 3-methylamino-2-phenylpropyltin triethoxide, ethylaminomethyloxymethyltin triethoxide, methylaminomethylthiomethyltin triethoxide, and the like.

Concrete examples of the organotin compound (B), expressed by the general formula (I), wherein X, Y, and Z each respectively represents a halogen atom, may include o-(1-aminoethyl)phenyltin tribromide, o-(aminomethyl) phenyltin tribromide, o-(1-aminoethyl)phenyltin trichloride, o-(aminomethyl)phenyltin trichloride, 3-aminopropyltin tribromide, 3-aminopropyltin trichloride, 3-aminopropyltin tribromide, 4-aminobutyltin tribromide, 4-aminobutyltin trichloride, 5-aminopentyltin tribromide, 5-aminopentyltin trichloride, 2-(1-aminoethyl)cyclohexyltin tribromide, 2-(1-aminoethyl)naphthalene-3-yltin tribromide, 2-(1-aminoethyl)furan-3-yltin tribromide, 2-(1-aminoethyl) thiophene-3-yltin tribromide, 3-ethylamino-2-methylpropyltin tribromide, 3-methylamino-2-phenylpropyltin tribromide, ethylaminomethyloxymethyltin tribromide, methylaminomethylthiomethyltin tribromide, 2-(1-aminoethyl)cyclohexyltin trichloride, 2-(1-aminoethyl) naphthalene-3-yltin trichloride, 2-(1-aminoethyl)furan-3-yltin trichloride, 2-(1-aminoethyl)thiophene-3-yltin trichloride, 3-ethylamino-2-methylpropyltin trichloride, 3-methylamino-2-phenylpropyltin chloride, ethylaminomethyloxymethyltin trichloride, methylaminomethylthiomethyltin trichloride, and the like.

Concrete examples of the organotin compound (C), expressed by the general formula (I), wherein X, Y, and Z each respectively represents an alkylthio group, may include o-(1-aminoethyl)phenyltin tri(thiomethoxide), o-(1-aminoethyl)phenyltin tri(thioethoxide), o-(1-aminoethyl) phenyltin tri(n-thiopropoxide), o-(1-aminoethyl)phenyltin tri(i-thiopropoxide), o-(1-aminoethyl)phenyltin tri(n-thiobutoxide), o-(1-aminoethyl)phenyltin tri(i-thiobutoxide), o-(1-aminoethyl)phenyltin tri(sec-thiobutoxide), o-(aminomethyl)phenyltin tri(thiomethoxide), o-(aminomethyl)phenyltin tri(thioethoxide), o-(aminomethyl)phenyltin tri(n-thiopropoxide), o-(aminomethyl)phenyltin tri(i-thiopropoxide), o-(1-aminoethyl)phenyltin tri(n-thiobutoxide), o-(aminomethyl)phenyltin tri(i-thiobutoxide), o-(aminomethyl)phenyltin tri(sec-thiobutoxide), 3-aminobutyltin tri(thiomethoxide), 3-aminobutyltin tri(thioethoxide), 3-aminobutyltin tri(n-thiopropoxide), 3-aminobutyltin tri(i-thiopropoxide), 3-aminobutyltin tri(n-thiobutoxide), 3-aminobutyltin tri(i-thiobutoxide), 3-aminobutyltin tri(sec-thiobutoxide), 3-aminopropyltin tri(thiomethoxide), 3-aminopropyltin tri(thioethoxide), 3-aminobutyltin tri(n-thiopropoxide), 3-aminopropyltin tri(i-thiopropoxide), 3-aminoprop yltin tri (n-thiobutoxide), 3-aminopropyltin tri(i-thiobutoxide), 3-aminopropyltin tri(sec-thiobutoxide), 4-aminopentyltin tri (thiomethoxide), 4-aminopentyltin tri(thioethoxide), 4-aminopentyltin tri(n-thioprop oxide), 4-aminopentyltin tri (i-thiopropoxide), 4-aminopentyltin tri(n-thiobutoxide), 4-aminopentyltin tri(i-thiobutoxide), 4-aminopentyltin tri (sec-thiobutoxide), 4-aminobutyltin tri(thiomethoxide), 4-aminobutyltin tri(thioethoxide), 4-aminobutyltin tri(n-thiopropoxide), 4-aminobutyltin tri(i-thiopropoxide), 4-aminopentyltin tri(n-thiobutoxide), 4-aminobutyltin tri(i-thiobutoxide), 4-aminobutyltin tri(sec-thiobutoxide), 5-aminohexyltin tri(thiomethoxide), 5-aminohexyltin tri (thioethoxide), 5-aminohexyltin tri(n-thiopropoxide), 5-aminohexyltin tri(i-thiopropoxide), 5-aminohexyltin tri(n-thiobutoxide), 5-aminohexyltin tri(i-thiobutoxide), 5-aminohexyltin tri(sec-thiobutoxide), 5-aminopentyltin tri (thiomethoxide), 5-aminopentyltin tri(thioethoxide), (aminomethyl)butyltin tri(n-thiopropoxide), 5-aminopentyltin tri(i-thiopropoxide), 5-aminohexyltin tri (n-thiobutoxide), 5-aminopentyltin tri(i-thiobutoxide), (aminomethyl)butyltin tri(sec-thiobutoxide), 2-(1-aminoethyl)cyclohexyltin tri(thioethoxide), 2-(1-aminoethyl)naphthalene-3-yltin tri(thioethoxide), 2-(1-aminoethyl)furan-3-yltin tri(thioethoxide), 2-(1-aminoethyl) thiophene-3-yltin tri(thioethoxide), 3-ethylamino-2-methylpropyltin tri(thioethoxide), 3-methylamino-2-phenylpropyltin tri(thioethoxide), ethylaminomethyloxymethyltin tri(thioethoxide), methylaminomethylthiomethyltin tri(thioethoxide), and the like.

Concrete examples of the organotin compound (D), expressed by the general formula (I), wherein X represents an alkyl group, Y and Z each respectively represents an alkoxyl group, may include o-(1-aminoethyl)phenyl-methyltin di(methoxide), o-(1-aminoethyl)phenyl-methyltin di(ethoxide), o-(1-aminoethyl)phenyl-methyltin di(n-propoxide), o-(1-aminoethyl)phenyl-methyltin di(i-propoxide), o-(1-aminoethyl)phenyl-methyltin di(n-butoxide), o-(1-aminoethyl)phenyl-methyltin di(i- butoxide), o-(1-aminoethyl)phenyl-methyltin di(sec-butoxide), o-(aminomethyl)phenylmethyltin di(methoxide), o-(aminomethyl)phenyl-methyltin di(ethoxide), o-(aminomethyl)phenylmethyltin di(n-propoxide), o-(aminomethyl)phenyl-methyltin di(i-propoxide), o-(1-aminoethyl)phenyl-methyltin di(n-butoxide), o-(aminomethyl)phenyl-methyltin di(i-butoxide), o-(aminomethyl)phenyl-methyltin di(sec-butoxide), (3-aminobutyl)methyltin di(methoxide), (3-aminobutyl)methyltin di(ethoxide), (3-aminobutyl)methyltin di(n-propoxide), (3-aminobutyl)methyltin di(i-propoxide), (3-aminobutyl)methyltin di(n-butoxide), (3-aminobutyl)methyltin di(i-butoxide), (3-aminobutyl)methyltin di(sec-butoxide), (3-aminopropyl)methyltin di(methoxide), (3-aminopropyl)methyltin di(ethoxide), (3-aminopropyl)methyltin di(n-prop oxide), (3-aminopropyl)methyltin di(i-propoxide), (3-aminopropyl)methyltin di(n-butoxide), (3-aminopropyl)methyltin di(i-butoxide), (3-aminopropyl)methyltin di(sec-butoxide), (4-aminopentyl)methyltin di(methoxide), (4-aminopentyl)methyltin di(ethoxide), (4-aminopentyl)methyltin di(n-propoxide), (4-aminopentyl)methyltin di(i-propoxide), (4-aminopentyl)methyltin di(n-butoxide), (4-aminopentyl)methyltin di(i-butoxide), (4-aminopentyl)methyltin di(sec-butoxide), (4-aminobutyl)methyltin di(methoxide), (4-aminobutyl)methyltin di(ethoxide), (4-aminobutyl)methyltin di(n-propoxide), (4-aminobutyl)methyltin di(i-propoxide), (4-aminobutyl)methyltin di(n-butoxide), (4-aminobutyl)methyltin di(i-butoxide), (4-aminobutyl)methyltin di(sec-butoxide), (5-aminohexyl)methyltin di(methoxide), (5-aminohexyl)methyltin di(ethoxide), (5-aminohexyl)methyltin di(n-propoxide), (5-aminohexyl)methyltin di(i-propoxide), (5-aminohexyl)methyltin di(n-butoxide), (5-hexyl)methyltin di(i-butoxide), (5-aminohexyl)methyltin di(sec-butoxide), (5-aminopentyl)methyltin di(methoxide), (5-aminopentyl)ethyltin di(ethoxide), (5-aminopentyl)methyltin di(n-propoxide), (5-aminopentyl)methyltin di(i-propoxide), 5-aminohexyl-methyltin di(n-butoxide), (5-aminopentyl)methyltin di(i-butoxide), (5-aminopentyl)methyltin di(sec-butoxide), o-(1-aminoethyl)phenyl-ethyltin di(methoxide), o-(1-aminoethyl)phenyl-ethyltin di(ethoxide), o-(1-aminoethyl)phenyl-ethyltin di(n-propoxide), o-(1-aminoethyl)phenyl-ethyltin di(i-propoxide), o-(1-aminoethyl)phenyl-ethyltin di(n-butoxide), o-(1-aminoethyl)phenyl-ethyltin di(i-butoxide), o-(1-aminoethyl)phenyl-ethyltin di(sec-butoxide), o-(aminomethyl)phenyl-ethyltin di(methoxide), o-(aminomethyl)phenyl-ethyltin di(ethoxide), o-(aminomethyl)phenyl-ethyltin di(n-propoxide), o-(aminomethyl)phenyl-ethyltin di(i-propoxide), o-(1-aminoethyl)phenyl-ethyltin di(n-butoxide), o-(aminomethyl)phenyl-ethyltin di(i-butoxide), o-(aminomethyl)phenyl-ethyltin di(sec-butoxide), (3-aminobutyl)ethyltin di(methoxide), (3-aminobutyl)ethyltin di(ethoxide), (3-aminobutyl)ethyltin di(n-propoxide), (3-aminobutyl)ethyltin di(i-propoxide), (3-aminobutyl)ethyltin di(n-butoxide), (3-aminobutyl)ethyltin di(i-butoxide), (3-aminobutyl)ethyltin di(sec-butoxide), (3-aminopropyl)ethyltin di(methoxide), (3-aminopropyl)ethyltin di(ethoxide), (3-aminopropyl)ethyltin di(n-propoxide), (3-aminopropyl)ethyltin di(i-propoxide), (3-aminopropyl)ethyltin di(n-butoxide), (3-aminopropyl)ethyltin di(i-butoxide), (3-aminopropyl)ethyltin di(sec-butoxide), (4-aminopentyl)ethyltin di(methoxide), (4-aminopentyl)ethyltin di(ethoxide), (4-aminopentyl)ethyltin di(n-propoxide), (4-aminopentyl)ethyltin di(i-propoxide), (4-aminopentyl)ethyltin di(n-butoxide), (4-aminopentyl)ethyltin di(i-butoxide), (4-aminopentyl)ethyltin di(sec-butoxide), (4-aminobutyl)ethyltin di(methoxide), (4-aminobutyl)ethyltin di(ethoxide), (4-aminobutyl)ethyltin di(n-propoxide), (4-aminobutyl)ethyltin di(i-propoxide), (4-aminobutyl)ethyltin di(n-butoxide), (4-aminobutyl)ethyltin di(i-butoxide), (4-aminobutyl)ethyltin di(sec-butoxide), (5-aminohexyl)ethyltin di(methoxide), (5-aminohexyl)ethyltin di(ethoxide), (5-aminohexyl)ethyltin di(n-propoxide), (5-aminohexyl)ethyltin di(i-propoxide), (5-aminohexyl)ethyltin di(n-butoxide), (5-aminohexyl)ethyltin di(i-butoxide), (5-aminohexyl)ethyltin di(sec-butoxide), (5-aminohexyl)ethyltin di(methoxide), (5-aminohexyl)methyltin di(ethoxide), (5-aminohexyl)ethyltin di(n-propoxide), (5-aminohexyl)ethyltin di(i-propoxide), (5-aminohexyl)ethyltin di(n-butoxide), (5-aminohexyl)ethyltin di(i-butoxide), (5-aminohexyl)ethyltin di(sec-butoxide), (2-(1-aminoethyl)cyclohexyl)ethyltin di(ethoxide), (2-(1-aminoethyl)naphthalene-3-yl)ethyltin di(ethoxide), (2-(1-aminoethyl)furan-3-yl)ethyltin di(ethoxide), (2-(1-aminoethyl)thiophene-3-yl)ethyltin di(ethoxide), (3-ethylamino-2-methylpropyl)ethyltin di(ethoxide), (3-methylamino-2-phenylpropyl)ethyltin di(ethoxide), (ethylaminomethyloxymethyl)ethyltin di(ethoxide), (methylaminomethylthiomethyl)ethyltin di(ethoxide), and the like.

Concrete examples of the organotin compound (E), expressed by the general formula (I), wherein X represents an alkyl group, and Y and Z each respectively represents a halogen atom, may include o-(aminomethyl)phenyl-methyltin dibromide, o-(aminomethyl)phenyl-methyltin dibromide, o-(1-aminoethyl)phenyl-methyltin dichloride, o-(aminomethyl)phenyl-methyltin dichloride, (3-aminopropyl)methyltin dibromide, (3-aminopropyl)methyltin dichloride, (3-aminopropyl)methyltin dibromide, (3-aminopropyl)methyltin dichloride, (4-aminobutyl)methyltin dibromide, (4-aminobutyl)methyltin dichloride, (4-aminobutyl)methyltin dibromide, (4-aminobutyl)methyltin dichloride, (5-aminopentyl)methyltin dibromide, (5-aminopentyl)methyltin dichloride, (5-aminopentyl)methyltin dibromide, (5-aminopentyl)methyltin dichloride, o-(aminomethyl)phenyl-ethyltin dibromide, o-(aminomethyl)phenyl-ethyltin dibromide, o-(aminomethyl)phenyl-ethyltin dichloride, o-(aminomethyl)phenyl-methyltin dichloride, (3-aminopropyl)ethyltin dibromide, (3-aminopropyl)methyltin dichloride, (3-aminopropyl)ethyltin dibromide, (3-aminopropyl)ethyltin dichloride, (4-aminobutyl)ethyltin dibromide, (4-aminobutyl)ethyltin dichloride, (4-aminobutyl)ethyltin dibromide, (4-aminobutyl)ethyltin dichloride, (5-aminopentyl)ethyltin dibromide, (5-aminopentyl)ethyltin dichloride, (5-aminopentyl)ethyltin dibromide, (5-amino pentyl )ethyltin dichloride, (2-(1-aminoethyl)cyclohexyl)ethyltin dibromide, (2-(1-aminoethyl)naphthalene-3-yl)ethyltin dichloride, (2-(1-aminoethyl)furan-3-yl)ethyltin dibromide, (2-(1-aminoethyl)thiophene-3-yl)ethyltin dichloride, (3-ethylamino-2-methylpropyl)ethyltin dibromide, (3-methylamino-2-phenylpropyl)ethyltin dichloride, (ethylaminomethyloxymethyl)ethyltin dibromide, (methylaminomethylthiomethyl)ethyltin dichloride, and the like.

Concrete examples of the organotin compound (F), expressed by the general formula (I), wherein X represents an alkyl group, and Y and Z each respectively represents an alkylthio group, may include o-(1-aminoethyl)phenyl-methyltin di(thiomethoxide), o-(1-aminoethyl)phenylmethyltin di(thioethoxide), o-(1-aminoethyl)phenyl-methyltin di(n-thiopropoxide), o-(1-aminoethyl)phenyl-methyltin di(i-thiopropoxide), o-(1-aminoethyl)phenyl-methyltin di(n-thiobutoxide), o-(1-aminoethyl)phenyl-methyltin di(i-thiobutoxide), o-(aminoethyl)phenyl-methyltin di(sec-thiobutoxide), o-(aminomethyl)phenyl-methyltin di(thiomethoxide), o-(aminomethyl)phenyl-methyltin di(thioethoxide), o-(aminomethyl)phenyl-methyltin di(n-thiopropoxide), o-(aminomethyl)phenyl-methyltin di(i-thiopropoxide), o-(aminomethyl)phenyl-methyltin di(n-thiobutoxide), o-(aminomethyl)phenyl-methyltin di(i-thiobutoxide), o-(aminomethyl)phenyl-methyltin di(sec-thiobutoxide), (4-aminobutyl)methyltin di(thiomethoxide), (4-aminobutyl)methyltin di(thioethoxide), (4-aminobutyl)methyltin di(n-thiopropoxide), (4-aminobutyl)methyltin di(i-thiopropoxide), (4-aminobutyl)methyltin di(n-thiobutoxide), (4-aminobutyl)methyltin di(i-thiobutoxide), (4-aminobutyl)methyltin di(sec-thiobutoxide), (3-amino propyl )methyltin di(thio methoxide), (3-aminopropyl)methyltin di(thioethoxide), (3-aminopropyl)methyltin di(n-thiopropoxide), (3-aminopropyl)methyltin di(i-thiopropoxide), (3-aminopropyl)methyltin di(n-thiobutoxide), (3-aminopropyl)methyltin di(i-thiobutoxide), (3-aminopropyl )methyltin di(sec-thiobutoxide), (4-aminopentyl)methyltin di(thiomethoxide), (4-aminopentyl)methyltin di(thioethoxide), (4-aminopentyl)methyltin di(n-thiopropoxide), (4-aminopentyl)methyltin di(i-thiopropoxide), (4-aminopenty l)methyltin di(n-thiobutoxide), (4-aminopentyl)methyltin di(i-thiobutoxide), (4-aminopentyl)methyltin di(sec-thiobutoxide), (4-aminobutyl)methyltin di(thiomethoxide), (4-aminobutyl)methyltin di(thioethoxide), (4-aminobutyl)methyltin di(n-thiopropoxide), (4-aminobutyl)methyltin di(i-thiopropoxide), (4-aminobutyl)methyltin di(n-thiobutoxide), (4-aminobutyl)methyltin di(i-thiobutoxide), (4-aminobutyl)methyltin di(sec-thiobutoxide), (5-aminohexyl)methyltin di(thiomethoxide), (5-aminohexyl)methyltin di(thioethoxide), (5-aminohexyl)methyltin di(n-thiopropoxide), (5-aminohexyl)methyltin di(i-thiopropoxide), (5-aminohexyl)methyltin di(n-thiobutoxide), (5-aminohexyl)methyltin di(i-thiobutoxide), (5-aminohexyl)methyltin di(sec-thiobutoxide), (5-aminopentyl)methyltin di(thiomethoxide), (5-aminopentyl)methyltin di(thioethoxide), (5-aminopentyl)methyltin di(n-thiopropoxide), (5-aminopentyl)methyltin di(i-thiopropoxide), (5-aminopentyl)methyltin di(n-thiobutoxide), (5-aminopentyl)methyltin di(i-thiobutoxide), (5-aminopentyl)methyltin di(sec-thiobutoxide), o-(1-aminoethyl)phenyl-ethyltin di(thiomethoxide), o-(1-aminoethyl)phenyl-ethyltin di(thioethoxide), o-(1-aminoethyl)phenyl-ethyltin di(n-thiopropoxide), o-(1-aminoethyl)phenyl-ethyltin di(i-thiopropoxide), o-(1-aminoethyl)phenyl-ethyltin di(n-thiobutoxide), o-(1-aminoethyl)phenyl-ethyltin di(i-thiobutoxide), o-(1-aminoethyl)phenyl-ethyltin di(sec-thiobutoxide), o-(aminomethyl)phenyl-ethyltin di(thiomethoxide), o-(aminomethyl)phenyl-ethyltin di(thioethoxide), o-(aminomethyl)phenyl-ethyltin di(n-thiopropoxide), o-(aminomethyl)phenyl-ethyltin di(i-thiopropoxide), o-(1-aminoethyl)phenyl-ethyltin di(n-thiobutoxide), o-(aminomethyl)phenyl-ethyltin di(i-thiobutoxide), o-(aminomethyl)phenyl-ethyltin di(sec-thiobutoxide), (3-aminobutyl)ethyltin di(thiomethoxide), (3-aminobutyl)ethyltin di(thioethoxide), (3-aminobutyl)ethyltin di(n-thiopropoxide), (3-aminobutyl)ethyltin di(i-thiopropoxide), (3-aminobutyl)ethyltin di(n-thiobutoxide), (3-aminobutyl) ethyltin di(i-thiobutoxide), (3-aminobutyl)ethyltin di(sec-thiobutoxide), (3-aminopropyl)ethyltin di(thiomethoxide), (3-aminopropyl)ethyltin di(thioethoxide), (3-aminopropyl)ethyltin di(n-thiopropoxide), (3-aminopropyl)ethyltin di(i-thiopropoxide), (3-aminopropyl)ethyltin di(n-thiobutoxide), (3-aminopropyl)ethyltin di(i-thiobutoxide), (3-aminopropyl)ethyltin di(sec-thiobutoxide), (4-aminopentyl)ethyltin di(thiomethoxide), (4-aminopentyl)ethyltin di(thioethoxide), (4-aminopentyl)ethyltin di(n-thiopropoxide), (4-aminopentyl)ethyltin di(i-thiopropoxide), (4-aminopentyl)ethyltin di(n-thiobutoxide), (4-aminopentyl)ethyltin di(i-thiobutoxide), (4-aminopentyl)ethyltin di(sec-thiobutoxide), (4-aminobutyl)ethyltin di(thiomethoxide), (4-aminobutyl)ethyltin di(thioethoxide), (4-aminobutyl)ethyltin di(n-thiopropoxide), (4-aminobutyl)ethyltin di(i-thiopropoxide), (4-aminobutyl)ethyltin di(n-thiobutoxide), (4-aminobutyl)ethyltin di(i-thiobutoxide), (4-aminobutyl)ethyltin di(sec-thiobutoxide), (5-aminohexyl)ethyltin di(thiomethoxide), (5-aminohexyl)ethyltin di(thioethoxide), (5-aminohexyl)ethyltin di(n-thiopropoxide), (5-aminohexyl)ethyltin di(i-thiopropoxide), (5-aminohexyl)ethyltin di(n-thiobutoxide), (5-aminohexyl)ethyltin di(i-thiobutoxide), (5-aminohexyl)ethyltin di(sec-thiobutoxide), (5-aminopentyl)ethyltin di(thiomethoxide), (5-aminopentyl)ethyltin di(thioethoxide), (5-aminopentyl)ethyltin di(n-thiopropoxide), (5-aminopentyl)ethyltin di(i-thiopropoxide), (5-aminopentyl)ethyltin di(n-thiobutoxide), (5-aminopentyl)ethyltin di(i-thiobutoxide), (5-aminopentyl)ethyltin di(sec-thiobutoxide), (2-(1-aminoethyl)cyclohexyl)ethyltin di(thioethoxide), (2-(1-aminoethyl)naphthalene-3-yl)ethyltin di(thioethoxide), (2-(1-aminoethyl)furan-3-yl)ethyltin di(thioethoxide), (2-(1-aminoethyl)thiophene-3-yl)ethyltin di(thioethoxide), (3-ethylamino-2-methylpropyl)ethyltin di(thioethoxide), (3-methylamino-2-phenylpropyl)ethyltin di(thioethoxide), (ethylaminomethyloxymethyl)ethyltin di(thioethoxide), (methylaminomethylthiomethyl)ethyltin di(thioethoxide), and the like.

Concrete examples of the organotin compound (G), expressed by the general formula (I), wherein X represents an alkyl group, Y represents an alkoxyl group, and Z represents a halogen atom, may include o-(1-aminoethyl)phenyl-methyl-methoxytin chloride, o-(1-aminoethyl)phenyl-methyl-ethoxytin chloride, o-(1-aminoethyl)phenyl-methyl-n-propoxytin chloride, o-(1-aminoethyl)phenyl-methyl-i-propoxytin chloride, o-(1-aminoethyl)phenyl-methyl-n-butoxytin chloride, o-(1-aminoethyl)phenyl-methyl-i-butoxytin chloride, o-(1-aminoethyl)phenyl-methyl-sec-butoxytin chloride, o-(1-aminoethyl)phenyl-ethyl-methoxytin chloride, o-(1-aminoethyl)phenyl-ethyl-ethoxytin chloride, o-(1-aminoethyl)phenyl-ethyl n-propoxytin chloride, o-(1-aminoethyl)phenyl-ethyl-i-propoxytin chloride, o-(1-aminoethyl)phenyl-ethyl-n-butoxytin chloride, o-(1-aminoethyl)phenyl-ethyl-i-butoxytin chloride, o-(1-aminoethyl)phenyl-ethyl-sec-butoxytin chloride, (4-aminopentyl)methyl-methoxytin chloride, (1-aminoethyl)propyl-methyl-ethoxytin chloride, (4-aminopentyl)methyl-n-propoxytin chloride, (4-aminopentyl)methyl-i-propoxytin chloride, (4-aminopentyl)methyl-n-butoxytin chloride, (4-aminopentyl)methyl-i-butoxytin chloride, (4-aminopentyl)methyl-sec-butoxytin chloride, (4-aminopentyl)ethyl-methoxytin chloride, (4-aminopentyl)ethyl-ethoxytin chloride, (4-aminopentyl)ethyl-n-propoxytin chloride, (4-aminopentyl)ethyl-i-propoxytin chloride, (4-aminopentyl)ethyl-n-butoxytin chloride, (4-aminopentyl)ethyl-i-butoxytin chloride, (4-aminopentyl)ethyl-sec-butoxytin chloride, o-(1-aminoethyl)phenylmethyl-methoxytin bromide, o-(1-aminoethyl)phenyl-methyl-ethoxytin bromide, o-(1-aminoethyl)phenyl-methyl-n-propoxytin bromide, o-(1-aminoethyl)phenyl-methyl-i-propoxytin bromide, o-(1-aminoethyl)phenyl-methyl-n-butoxytin bromide, o-(1-aminoethyl)phenyl-methyl-i-butoxytin bromide, o-(1-aminoethyl)phenyl-methyl-sec-butoxytin bromide, o-(1-aminoethyl)phenyl-ethyl-methoxytin bromide, o-(1-aminoethyl)phenyl-ethyl-ethoxytin bromide, o-(1-aminoethyl)phenyl-ethyl-n-propoxytin bromide, o-(1-aminoethyl)phenyl-ethyl-i-propoxytin bromide, o-(1-aminoethyl)phenyl-ethyl-n-butoxytin bromide, o-(1-aminoethyl)phenyl-ethyl-i-butoxytin bromide, o-(1-aminoethyl)phenyl-ethyl-sec-butoxytin bromide, (4-aminopentyl)methyl-methoxytin bromide, (4-aminopentyl)methyl-ethoxytin bromide, (4-aminopentyl)methyl-n-propoxytin bromide, (4-aminopentyl)methyl-i-propoxytin bromide, (4-aminopentyl)methyl-n-butoxytin bromide, (4-aminopentyl)methyl-i-butoxytin bromide, (4-aminopentyl)methyl-sec-butoxytin bromide, (4-aminopentyl)ethyl-methoxytin bromide, (1-aminopentyl)ethyl-ethoxytin bromide, (4-aminopentyl)ethyl-n-propoxytin bromide, (4-aminopentyl)ethyl-i-propoxytin bromide, (4-aminopentyl)ethyl-n-butoxytin bromide, (4-aminopentyl)ethyl-i-butoxytin bromide, (4-aminopentyl)ethyl-sec-butoxytin bromide, (2-(1-aminoethyl)cyclohexyl)ethyl-ethoxytin chloride, (2-(1-aminoethyl)naphthalene-3-yl)ethyl-n-propoxytin bromide, (2-(1-aminoethyl)furan-3-yl)ethyl-ethoxytin chloride, (2-(1-aminoethyl)thiophene-3-yl)ethyl-n-propoxytin chloride, (3-ethylamino-2-methylpropyl)ethyl-ethoxytin bromide, (3-methylamino-2-phenylpropyl)ethyl-n-propoxytin chloride, (ethylaminomethyloxymethyl)ethyl-ethoxytin bromide, (methylaminomethylthiomethyl)ethyl-n-propoxytin chloride, and the like.

Concrete examples of the organotin compound (H), expressed by the general formula (I), wherein X represents an alkyl group, Y represents an alkoxyl group, and Z represents an alkylthio group, may include o-(1-aminoethyl)phenyl-methyl-thiomethyltin methoxide, o-(1-aminoethyl)phenyl-methyl-thiomethyltin ethoxide, o-(1-aminoethyl)phenyl-methyl-thiomethyltin n-propoxide, o-(1-aminoethyl)phenyl-methyl-thiomethyltin i-propoxide, o-(1-aminoethyl)phenyl-methyl-thiomethyltin n-butoxide, o-(1-aminoethyl)phenyl-methyl-thiomethyltin i-butoxide, o-(1-aminoethyl)phenyl-methyl-thiomethyltin sec-butoxide, o-(aminomethyl)phenyl-methyl thiomethyltin methoxide, o-(aminomethyl)phenyl-methyl thiomethyltin ethoxide, o-(aminomethyl)phenyl-methyl thiomethyltin n-propoxide, o-(aminomethyl)phenyl-methyl thiomethyltin i-propoxide, o-(aminomethyl)phenyl-methyl thiomethyltin n-butoxide, o-(aminomethyl)phenyl-methyl thiomethyltin i-butoxide, o-(aminomethyl)phenyl-methyl thiomethyltin sec-butoxide, (3-aminobutyl)methyl-thiomethyltin methoxide, (3-aminobutyl)methyl-thiomethyltin ethoxide, (3-aminobutyl)methyl-thiomethyltin n-propoxide, (3-aminobutyl)methyl-thiomethyltin di(i-propoxide), (3-aminobutyl)methyl-thiomethyltin n-butoxide, (3-aminobutyl)methyl-thiomethyltin i-butoxide, (3-aminobutyl)methyl-thiomethyltin sec-butoxide, (3-aminopropyl)methyl-thiomethyltin methoxide, (3-aminopropyl)methyl-thiomethyltin ethoxide, (3-aminopropyl)methyl-thiomethyltin n-propoxide, (3-aminopropyl)methyl-thiomethyltin i-propoxide, (3-aminopropyl)methyl-thiomethyltin n-butoxide, (3-aminopropyl)methyl-thiomethyltin i-butoxide, (3-aminopropyl)methyl-thiomethyltin sec-butoxide, (4-aminobutyl)methyl-thiomethyltin methoxide, (1-aminoethyl)propyl-methyl-thiomethyltin ethoxide, (4-aminopentyl)methyl-thiomethyltin n-propoxide, (4-aminopentyl)methyl-thiomethyltin i-propoxide, (4-aminopentyl)methyl-thiomethyltin n-butoxide, (4-aminopentyl)methyl-thiomethyltin i-butoxide, (4-aminopentyl)methyl-thiomethyltin sec-butoxide, (4-aminobutyl)methyl-thiomethyltin methoxide, (4-aminobutyl)methyl-thiomethyltin ethoxide, (4-aminobutyl)methyl-thiomethyltin n-propoxide, (4-aminobutyl)methyl-thiomethyltin i-propoxide, (4-aminobutyl)methyl-thiomethyltin n-butoxide, (4-aminobutyl)methyl-thiomethyltin i-butoxide, (4-aminobutyl)methyl-thiomethyltin sec-butoxide, (5-aminohexyl)methyl-thiomethyltin methoxide, (5-aminohexyl)methyl-thiomethyltin ethoxide, (5-aminohexyl)methyl-thiomethyltin n-propoxide, (5-aminohexyl)methyl-thiomethyltin i-propoxide, (5-aminohexyl)methyl-thiomethyltin n-butoxide, (5-aminohexyl)methyl-thiomethyltin i-butoxide, (5-aminohexyl)methyl-thiomethyltin sec-butoxide, (5-aminopentyl)methyl-thiomethyltin methoxide, (5-aminopentyl)methyl-thiomethyltin ethoxide, (5-aminopentyl)methyl-thiomethyltin n-propoxide, (5-aminopentyl)methyl-thiomethyltin i-propoxide, (5-aminopentyl)methyl-thiomethyltin n-butoxide, (5-aminopentyl)methyl-thiomethyltin i-butoxide, (5-aminopentyl)methyl-thiomethyltin sec-butoxide, o-(1-aminoethyl)phenyl-ethyl-thiomethyltin methoxide, o-(1-aminoethyl)phenyl-ethyl-thiomethyltin ethoxide, o-(1-aminoethyl)phenyl-ethyl-thiomethyltin n-propoxide, o-(1-aminoethyl)phenyl-ethyl-thiomethyltin i-propoxide, o-(1-aminoethyl)phenyl-ethyl-thiomethyltin n-butoxide, o-(1-aminoethyl)phenyl-ethyl-thiomethyltin i-butoxide, o-(1-aminoethyl)phenyl-ethyl-thiomethyltin sec-butoxide, (aminomethyl)phenyl-ethyl-thiomethyltin methoxide, o-(aminomethyl)phenyl-ethyl thiomethyltin ethoxide, o-(aminomethyl)phenyl-ethyl thiomethyltin n-propoxide, o-(aminomethyl)phenyl-ethyl thiomethyltin i-propoxide, o-(1-aminoethyl)phenyl-ethyl thiomethyltin n-butoxide, o-(aminomethyl)phenyl-ethyl thiomethyltin i-butoxide, o-(aminomethyl)phenyl-ethyl thiomethyltin sec-butoxide, (3-aminobutyl)ethyl-thiomethyltin methoxide, (3-aminobutyl)ethyl-thiomethyltin ethoxide, (3-aminobutyl)ethyl-thiomethyltin n-propoxide, (3-aminobutyl)ethyl-thiomethyltin i-propoxide, (3-aminobutyl)ethyl-thiomethyltin n-butoxide, (3-aminobutyl)ethyl-thiomethyltin i-butoxide, (3-aminobutyl)ethyl-thiomethyltin sec-butoxide, (3-aminopropyl)ethyl-thiomethyltin methoxide, (3-aminopropyl)ethyl-thiomethyltin ethoxide, (3-aminopropyl)ethyl-thiomethyltin n-propoxide, (3-aminopropyl)ethyl-thiomethyltin i-propoxide, (3-aminopropyl)ethyl-thiomethyltin n-butoxide, (3-aminopropyl)ethyl-thiomethyltin i-butoxide, (3-aminopropyl)ethyl-thiomethyltin sec-butoxide, (4-aminopentyl)ethyl-thiomethyltin methoxide, (3-aminopentyl)ethyl-thiomethyltin ethoxide, (4-aminopentyl)ethyl-thiomethyltin n-propoxide, (4-aminopentyl)ethyl-thiomethyltin i-propoxide, (4-aminopentyl)ethyl-thiomethyltin n-butoxide, (4-aminopentyl)ethyl-thiomethyltin i-butoxide, (4-aminopentyl)ethyl-thiomethyltin sec-butoxide, (4-aminobutyl)ethyl-thiomethyltin methoxide, (4-aminobutyl)ethyl-thiomethyltin ethoxide, (4-aminobutyl)ethyl-thiomethyltin n-propoxide, (4-aminobutyl)ethyl-thiomethyltin i-propoxide, (4-aminobutyl)ethyl-thiomethyltin n-butoxide, (4-aminobutyl)ethyl-thiomethyltin i-butoxide, (4-aminobutyl)ethyl-thiomethyltin sec-butoxide, (5-aminohexyl)ethyl-thiomethyltin methoxide, (5-aminohexyl)ethyl-thiomethyltin ethoxide, (5-aminohexyl)ethyl thiomethyltin n-propoxide, (5-aminohexyl)ethyl thiomethyltin i-propoxide, (5-aminohexyl)ethyl thiomethyltin n-butoxide, (5-aminohexyl)ethyl thiomethyltin i-butoxide, (5-aminohexyl)ethyl thiomethyltin sec-butoxide, (2-(1-aminoethyl)cyclohexyl)ethyl-thiomethyltin methoxide, (2-(1-aminoethyl)naphthalene-3-yl)ethyl-thioethyltin ethoxide, (2-(1-aminoethyl)furan-3-yl)ethyl-thioethyltin ethoxide, (2-(1-aminoethyl)thiophene-3-yl)ethyl-thioethyltin ethoxide, (3-ethylamino-2-methylpropyl)ethyl-thioethyltin ethoxide, (3-methylamino-2-phenylpropyl)ethyl-thioethyltin ethoxide, (ethylaminomethyloxymethyl)ethyl-thioethyltin ethoxide, (methylaminomethylthiomethyl)ethyl-thioethyltin ethoxide, and the like.

Concrete examples of the organotin compound (J), expressed by the general formula (I), wherein X represents an alkyl group, Y represents a halogen atom, and Z represents an alkylthio group, may include o-(1-aminoethyl) phenyl-methyl-thiomethoxytin chloride, o-(1-aminoethyl) phenyl-methyl-thioethoxytin chloride, o-(1-aminoethyl) phenyl-methyltin n-thiopropoxytin chloride, o-(1-aminoethyl)phenyl-methyl-i-thiopropoxytin chloride, o-(1-aminoethyl)phenyl-methyl-n-thiobutoxytin chloride, o-(1-aminoethyl)phenyl-methyl-i-thiobutoxytin chloride, o-(1-aminoethyl)phenyl-methyl-sec-thiobutoxytin chloride, o-(1-aminoethyl)phenyl-ethyl-thiomethoxytin chloride, o-(1-aminoethyl)phenyl-ethyl-thioethoxytin chloride, o-(1-aminoethyl)phenyl-ethyl-n-thiopropoxytin chloride, o-(1-aminoethyl)phenyl-ethyl-i-thiopropoxytin chloride, o-(1-aminoethyl)phenyl-ethyl-n-thiobutoxytin chloride, o-(1-aminoethyl)phenyl-ethyl-i-thiobutoxytin chloride, o-(1-aminoethyl)phenyl-ethyl-sec-thiobutoxytin chloride, (4-aminopentyl)methyl-thiomethoxytin chloride, (4-aminopentyl)methyl-thioethoxytin chloride, (4-aminopentyl)methyl-n-thiopropoxytin chloride, (4-aminopentyl)methyl-i-thiopropoxytin chloride, (4-aminopentyl)methyl-n-thiobutoxytin chloride, (4-aminopentyl)methyl-i-thiobutoxytin chloride, (4-aminopentyl)methyl-sec-thiobutoxytin chloride, (4-aminopentyl)ethyl-thiomethoxytin chloride, (4-aminopentyl)ethyl-thioethoxytin chloride, (4-aminopentyl)ethyl-n-thiopropoxytin chloride, (4-aminopentyl)ethyl-i-thiopropoxytin chloride, (4-aminopentyl)ethyl-n-thiobutoxytin chloride, (4-aminopentyl)ethyl-i-thiobutoxytin chloride, (4-aminopentyl)ethyl-sec-thiobutoxytin chloride, o-(1-aminoethyl)phenyl-methyl-thiomethoxytin bromide, o-(1-aminoethyl)phenyl-methyl-thioethoxytin bromide, o-(1-aminoethyl)phenyl-methyltin n-thiopropoxytin bromide, o-(1-aminoethyl)phenyl-methyl-i-thiopropoxytin bromide, o-(1-aminoethyl)phenyl-methyl-n-thiobutoxytin bromide, o-(1-aminoethyl)phenyl-methyl-i-thiobutoxytin bromide, o-(1-aminoethyl)phenyl-methyl-sec-thiobutoxytin bromide, o-(1-aminoethyl)phenyl-ethyl-thiomethoxytin bromide, o-(1-aminoethyl)phenyl-ethyl-thioethoxytin bromide, o-(1-aminoethyl)phenyl-ethyl-n-thiopropoxytin bromide, o-(1-aminoethyl)phenyl-ethyl-i-thiopropoxytin bromide, o-(1-aminoethyl)phenyl-ethyl-n-thiobutoxytin bromide, o-(1-aminoethyl)phenyl-ethyl-i-thiobutoxytin bromide, o-(1-aminoethyl)phenyl-ethyl-sec-thiobutoxytin bromide, (4-aminopentyl)methyl-thiomethoxytin bromide, (4-pentyl)methyl-thioethoxytin bromide, (4-aminopentyl)methyl-n-thio propoxytin bromide, (4-aminopentyl)methyl-i-thiopropoxytin bromide, (4-aminopentyl)methyl-n-thiobutoxytin bromide, (4-aminopentyl)methyl-i-thiobutoxytin bromide, (4-aminopentyl)methyl-sec-thiobutoxytin bromide, (4-aminopentyl)ethyl-thiomethoxytin bromide, (4-aminopentyl)ethyl-thioethoxytin bromide, (4-aminopentyl)ethyl-n-thiopropoxytin bromide, (4-aminopentyl)ethyl-i-thiopropoxytin bromide, (4-aminopentyl)ethyl-n-thiobutoxytin bromide, (4-aminopentyl)ethyl-i-thiobutoxytin bromide, (4-aminopentyl)ethyl-sec-thiobutoxytin bromide, (2-(1-aminoethyl)cyclohexyl)ethyl-thiomethyltin chloride, (2-(1-aminoethyl)naphthalene-3-yl) ethyl-thioethyltin bromide, (2-(1-aminoethyl)furan-3-yl) ethyl-thioethyltin bromide, (2-(1-aminoethyl)thiophene-3-yl)ethyl-thioethyltin chloride, (3-ethyiamino-2-methylpropyl)ethyl-thioethyltin bromide, (3-methylamino-2-phenylpropyl)ethyl-thioethyltin chloride, (ethylaminomethyloxymethyl)ethyl-thioethyltin bromide, (methylaminomethylthiomethyl)ethyl-thioethyltin chloride, and the like.

The aforementioned descriptions regarding to the organotin compound, expressed by the general formula (I), also applies correspondingly for the compound, expressed by the general formula (II).

It is possible to perform transesterification efficiently under a room temperature and an atmosphere pressure, in the presence of the catalyst comprising the organotin compound according to the present invention.

The ester compound, employed in transesterification according to the present invention, is not particularly limited. Concrete examples of an ester are combined a saturated or unsaturated, aliphatic or aromatic, carboxylic acid, which may contain a substituent group having 1~20 carbon atoms; and a saturated or unsaturated, aliphatic or aromatic alcohol, which may contain a substituent group, such that the number of the ester groups in the aforementioned compound is in the range of 1~6.

Further, the alcohol employed in transesterification, is not particularly limited; however, it is a compound in which the number of the hydroxyl groups, which may contain a substituent group, is in the range of 1~6. Concrete examples may include saturated aliphatic alcohols such as methanol, ethanol, propanol, butanol, octanol, laurylalcohol, stearylalcohol, cyclohexanol, ethylene glycol, propylene glycol, neopentyl glycol, butylene glycol, hexane diol, trimethylol propane, pentaerythritol, ditrimethylol propane, dipentaerythritol, and the like; aliphatic unsaturated alcohols such as an allylalcohol, butenylalcohol, octenylalcohol, and the like; aromatic substituted alcohols such as benzylalcohol, phenol, phenetole, phenoxy ethanol, phenoxy propanol, cresol, α-naphthol, β-naphthol, catechol, hydroquinone, bisphenol F, bisphenol A, and the like.

The amount of the catalyst, an organotin compound according to the present invention, employed in transesterification is not particularly limited; however, in the case when the usage amount (in molar units)of the ester compounds in the starting materials is less than that of the alcohol compounds, the amount of catalyst employed is 0.0001~0.1 mol per 1 mol of the ester group, and preferably, 0.005~0.05 mol per 1 mol of the ester group. In the case when the usage amount (in molar units)of the ester compounds in the starting materials is greater than that of the alcohol compounds, the amount of the catalyst used, per 1 mol of the hydroxyl group in the alcohol compounds in the transesterification, is 0.0001~0.1 mol, and preferably, 0.005~0.05 mol.

Normally, the transesterification according to the present invention is performed in the absence of a solvent; however, it is also possible to use a solvent that is inactive with respect to the reaction.

Examples of such solvents are: ether solvents such as dimethoxyethane, tetrahydrofuran, and the like; aliphatic hydrocarbon solvents such as hexane, cyclohexane, heptane, and the like; aromatic hydrocarbon solvents such as benzene, toluene, xylene, and the like; and aromatic halogenated hydrocarbon solvents such as chlorobenzene, dichlorobenzene, and the like.

In addition, the transesterification reaction, using the catalyst according to the present invention, is also applicable to a synthesis of an optically active compound, since it is possible to perform a transesterification without loss of the optical activity of chiral ester compound as the starting materials.

The methods for isolating and purifying the final product after the reaction are not particularly limited, and it is possible to perform the isolation or purification process according to an known method. For example, solvents and non-reactive materials can be removed after the reaction, and if necessary, washed and distilled. In addition, the organotin compound, employed as a catalyst, can be removed by means of the aforementioned processes, i.e., washing and distillation; the organotin compound can be also removed by means of filtration after undergoing reaction using an appropriate carrier such as a silica gel, activated clay, and the like. Additionally, the salvaged organotin compound is reusable.

The organotin compound according to the present invention is extremely useful as a catalyst, for production of an ester compound, and can provide the final product under less restrictive reaction conditions in a short period of time. Additionally, the organotin compound according to the present invention can be used as a stabilizer for plastics, additive for coating, or as a germicide.

In the following, the present invention is further described in detail, using the examples and comparative examples. Yields in the following examples and comparative examples are expressed in "mol percent".

EXAMPLE 1

Synthesis of o-(1-aminoethyl)phenyltin tris (methylethoxide)

(1) Synthesis of o-bromo-1-phenyl ethanol 5.25 g of o-bromophenone (28.9 mmol) and 30 ml of ethanol were introduced into a 100 ml eggplant type flask, and cooled to −78° C. Then, 1.09 g of sodium borohydride (28.9 mmol) was added dropwise, and then the mixture was stirred at 0° C. for 80 minutes. Subsequently, while maintaining the temperature at 0° C., 1N hydrogen chloride was added to adjust the concentration of the water layer to a pH=4. The resultant mixture was concentrated under reduced pressure, and successively distilled under reduced pressure, to yield 4.99 g of the final product at 132.0~136.5° C./23 mmHg (yield=85.8%).

(2) Synthesis of tetracyclohexyltin 28.9 g of magnesium flakes (1.19 mol) and 500 ml of diethylether were mixed together in a 1L three-neck flask, which was equipped with a stirrer, reflux condenser, and isobaric dropping funnel. Subsequently, 112 ml of cyclohexyl bromide (0.909 mol) was gradually added dropwise, and the mixture was stirred for 12 hours, to prepare cyclohexyl magnesium bromide. After 12 ml of tin tetrachloride (0.103 mol) was gradually added dropwise, the mixture was refluxed for 1.5 hours. Upon the completion of the reaction, 200 ml of water was added to the reaction mixture, followed by addition of 1N sulfuric acid to adjust the concentration of the water layer to a pH=5. After the organic layer, which had been obtained by separating the water layer from the mixture, was concentrated under reduced pressure, the solid precipitate was separated by filtration. The solid precipitate was then washed with acetone, and dried under a vacuum, to yield 37.6 g of the final product (yield=81.3%).

(3) Synthesis of tricyclohexyltin chloride 55.1 g of tetracyclohexyltin (122 mmol) and 50 ml of toluene were mixed together in a 200 ml eggplant type flask, and containing a stirrer. Then, 18.1 ml of tin tetrachloride (155 mmol) was added, and the mixture was refluxed for 3 hours. Upon completion of the reaction, the mixture was cooled to 0° C., and 30 ml of water and 50 ml of hexane were added. After the hexane layer was separated, the solid precipitate, which had been precipitated by removing the solvent under reduced pressure, was washed with 20 ml of acetonitrile, and dried under a vacuum, to yield 39.1 g of the final product (yield=59.5%).

(4) Synthesis of tricyclohexyl [o-(1-hydroxyethyl)phenyl] tin 10.1 g of o-bromo-1-phenylethanol (50.2 mmol) and 50 ml of diethylether were mixed together in a 500 ml two-neck flask, which was equipped with a stirrer and isobaric dropping funnel. To this mixture, 64.5 ml of hexane solution of n-butyl lithium was gradually added dropwise at −78° C. Subsequently, the temperature was raised to −30° C., and the mixture was stirred for 1 hour while maintaining the same temperature. The reaction mixture was cooled back to −78° C., and a mixed solvent solution containing 20.2 g of tricyclohexyltin chloride (50.1 mmol), 100 ml of hexane, and 50 ml of diethylether was added dropwise thereto. The temperature was raised back to −30° C., and the mixture was stirred for 12 hours at the same temperature. Upon completion of the reaction, 100 ml of water was added, and the organic substance was extracted three times, with 200 ml of diethylether for each. After the solvent was removed under reduced pressure, the oily product was purified by column chromatography on silica gel (for which, 50 g of silica gel, and a mixed solvent of hexane and diethylether, as a developing solvent, were employed) to yield 17.9 g of the final product (yield=73.0%).

(5) Synthesis of tricyclohexyl [o-(1-azidoethyl)phenyl]tin 997 mg of tricyclohexyl [o-(1-hydroxyethyl)phenyl]tin (2.04 mmol) and 20 ml of pyridine were mixed together in a 20 ml two-neck flask, then 269 mg of methane sulfonyl chloride (2.35 mmol) was added dropwise thereto. After the mixture was stirred for 22 hours at a room temperature, a brown-colored solid, which had been obtained by concentrating the reaction solution under reduced pressure, was dissolved in 10 ml of dimethylformamide. Subsequently, 10 ml of a dimethylformamide solution containing 354 mg of sodium azide (5.44 mmol) was added dropwise, and the mixture was then refluxed for 3 hours. After the mixture was cooled to 0° C., and 20 ml of water was added, the organic substance was extracted with 30 ml of ether three times. After the ether layer was washed with 30 ml of a saturated brine, and dried over sodium sulfate, the solvent was removed under reduced pressure to yield a crude product. The resultant crude product was purified by column chromatography on silica gel (for which, 50 g of silica gel, and hexane, as a devleoping solvent were employed) to yield 288 mg of the final product (0.559 mmol).

(6) Synthesis of tricyclohexyl [o-(1-aminoethyl)phenyl]tin

To the mixture of 486 mg of lithium aluminum hydride (12.3 mmol) and 20 ml of diethylether in a 100 ml two-neck flask, 20 ml of a diethylether solution containing 643 mg of tricyclohexyl[o-(1-azidoethyl)phenyl]tin (1.25 mmol) was added dropwise, followed by a heat-refluxing for 11.5 hours. Upon completion of the reaction, the organic layer was separated using 10 ml of water. After the ether layer was washed with 30 ml of a saturated brine and dried over sodium sulfate, the solvent was removed under reduced pressure to yield a crude product. The resultant crude product was purified by column chromatography on silica gel (for which, 25 g of silica gel, and hexane as a development solvent were employed) to yield 467 mg of the final product (yield=76.5%).

(7) Synthesis of o-(1-aminoethyl)phenyl]tin trichloride

To the mixture of 467 mg of tricyclohexyl [o-(1-aminoethyl)phenyl]tin (0.956 mmol) and 10 ml of n-hexane in a 20 ml two-neck flask, 260 mg of tin tetrachloride (0.997 mmol) was added dropwise, followed by stirring for 24 hours at a room temperature. After 5 ml of acetonitrile was added to the reaction mixture, the mixture was further stirred for 21 hours, and the acetonitrile layer in the lower aspect of the upper layer was separated. Subsequently, after the solvent was removed under reduced pressure, a residue was recrystallized from the acetonitrile, to yield 214 mg of the final pure product (yield=92.2%).

(8) Synthesis of o-(1-aminoethyl)phenyl]tin tris(methylethoxide)

To the 2-propanol solution of sodium methylethoxide in a 20 ml two-necked flask, prepared from 114 mg of sodium (4.97 mmol) and 20 ml of 2-propanol, 214 mg of o-(1-aminoethyl)phenyl]tin trichloride (0.881 mmol) was added dropwise, and the mixture was refluxed for 7 hours. After the solvent was removed under reduced pressure, 20 ml of n-hexane was added and the mixture was allowed to stand to facilitate removal of the supernatant. The solvent was removed under reduced pressure to yield 194 mg of the final product (yield=52.8%) as an amorphous solid.

EXAMPLE 2-1

Synthesis of 3-aminopropyltin tris(methylethoxide)

(1) Synthesis of tin tetra(methylethoxide)

Sodium isopropoxide was prepared from 2.3 g of sodium (0.1 mol) and 60 g of isopropylalcohol under a nitrogen atmosphere in a 200 ml four-neck flask equipped with a stirrer, reflux condenser, and isobaric dropping funnel. Then, 5.2 g of tin tetrachloride was gradually added dropwise to the sodium isopropoxide solution, and the mixture was refluxed for 2 hours. Upon completion of the reaction, the reaction mixture was cooled to a room temperature, then, the excess sodium isopropoxide was neutralized by the addition of 1N HCl. The NaCl obtained therefrom was then separated by filtration. The filtrate was concentrated under reduced pressure, and the residue was recrystallized from isopropylalcohol to yield 6.4 g of tin tetra(methylethoxide) (yield=90.6%).

(2) Synthesis of tris(methylethoxide)tin chloride 10.6 g of tin tetra(methylethoxide) (0.03 mol), prepared in the aforementioned example (1), and 100 ml of n-hexane were mixed together in a 200 ml four-neck flask equipped with a stirrer, reflux condenser, and isobaric dropping funnel. 30 ml of an n-hexane solution of 2.6 g of tin tetrachloride (0.01 mol) was added dropwise to the mixed solution at a rate that maintained the temperature of the reaction mixture below 5° C. Then, the mixture was refluxed for 10 hours. Subsequently, the reaction mixture was cooled, and a precipitated crystal was separated by filtration. The filtered crystal was then washed with n-hexane, and dried, to yield 8.4 g of tri(methylethoxide)tin chloride (yield=84.6%).

(3) Synthesis of tri(methylethoxide)tin hydride 33.2 g of tri(methylethoxide)tin chloride (0.1 mol), prepared in the aforementioned example (2), and 100 ml of tetrahydrofuran were mixed together in a 500 ml eggplant type flask. To this mixture 100 ml of a tetrahydrofuran solution of 10.5 g of sodium borohydride (0.27 mol) was gradually added dropwise while maintaining the temperature of the mixture below 10° C., the solution was then stirred at 10° C. for 4 hours. Upon completion of the reaction, acetone was added to the reaction mixture in order to decompose the excess sodium borohydride, and the resultant NaCl was then separated by filtration. The filtrate was concentrated under reduced pressure at below 30° C., to yield 19.7 g of tri(methylethoxide)tin hydride (yield=66.5%).

(4) Synthesis of 3-cyanoethyltin tris(methylethoxide)

5.94 g of tri(methylethoxide)tin hydride (0.01 mol), prepared in the aforementioned example (3), 5.3 g of acrylonitrile (0.1 mol), 300 mg of azobis(isobutyronitrile), and 50 ml of toluene were mixed together in a 200 ml eggplant type flask, and heated for 10 hours at 60° C. The reaction was judged to be complete after it was confirmed, by means of infrared absorption, that the absorption at 1800 $cm^{-1}$ of the nitrile group had disappeared. The solid that precipitated out in the reaction solution was then separated by filtration, and the filtrate was concentrated under reduced pressure, to yield 2.9 g of 3-cyanoethyltin tris(methylethoxide) (yield=81.6%).

(5) Synthesis of 3-aminopropyltin tris(methylethoxide)

0.57 g of lithium aluminium hydride (0.015 mol) and 20 ml of ether were mixed together in a 100 ml eggplant type flask. Subsequently, 20 ml of an ether solution of 3.5 g of the 3-cyanoethyltin tris(methylethoxide) (0.01 mol), prepared in the aforementioned example (4), was added dropwise to the mixed solution while maintaining the temperature of the mixture below 5° C. The reaction solution was then stirred for 1 hour at 5° C. Upon completion of the reaction, 3 ml of an aqueous solution of 20% sodium hydroxide and 50 ml of water were added to the reaction mixture, in order to decompose the excess lithium aluminium hydride. The ether layer was separated, washed with 50 ml of water, and concentrated under reduced pressure, to yield 2.7 g of 3-aminopropyltin tris(methylethoxide) (yield=77.1%).

EXAMPLE 2-2

Synthesis of 3-aminopropyltin tris(methylethoxide)

(1) Synthesis of triphenyltin hydride 3.9 g of sodium borohydride (0.1 mol) and 70 ml of monoglyme were mixed together in a 200 ml eggplant type flask and cooled to −10° C. 70 ml of a diglyme solution containing 10.0 g of triphenyltin chloride (0.026 mol) was added to this mixture dropwise for 30 minutes. Subsequently, the mixture was stirred for another 30 minutes at −10° C. Then diglyme was removed under a reduced pressure of greater than 1 mmHg at below 0° C. Then, the resultant residue was extracted with diethylether followed by concentration under reduced pressure to yield 9.1 g of the final product of triphenyltin hydride (yield=100%).

(2) Synthesis of 3-(triphenylstannyl)propionitrile 9.1 g of the triphenyltin hydride (0.026 mol), prepared in the aforementioned example (1), 2.8 g of acrylonitrile (0.052 mol), 85 mg of 2,2'-azobisisobutyronitrile, and 25 ml of toluene were mixed together in a 100 ml four-neck flask equipped with a stirrer and reflux condenser, and stirred while heating for 6 hours at 60° C. After it was confirmed by means of an IR spectrum that the absorption of Sn-H bonds had completely disappeared, a crystal precipitate was separated by filtration. The filtrate was then concentrated under reduced pressure to yield 10.5 g of the final product of 3-(triphenylstannyl)propionitrile (yield=100%).

(3) Synthesis of 3-(triphenylstannyl)propylamine 1.4 g of lithium aluminium hydride (0.038 mol) and 40 ml of tetrahydrofuran, (hereinafter, referred to as "THF"), were mixed together in a 200 ml four-neck flask equipped with a stirrer and isobaric dropping funnel. To the mixture 40 ml of a THF solution containing 10.1 g of 3-(triphenylstannyl) propionitrile (0.025 mol), prepared in the aforementioned example (2), was added dropwise for 1 hour at 0° C., and the reaction solution was stirred for 45 minutes at 0° C.

Subsequently, 4 ml of an aqueous solution of 5% sodium hydroxide and 20 ml of water were poured, and the mixture was stirred for 30 minutes at 0° C. Then, a solid precipitate was separated by filtration, and the filtrate was concentrated under reduced pressure. After the residue was extracted with 50 ml of toluene, and washed with 50 ml of water, toluene was removed under reduced pressure to yield 7.1 g of the final product of 3-(triphenylstannyl)propylamine (yield=70%).

(4) Synthesis of 3-(trichlorostannyl)propylamine 2.0 g of the 3-(triphenylstannyl)propylamine (4.9 mmol), prepared in the aforementioned example (3), and 25 ml of toluene were mixed together in a 100 ml eggplant type flask, and 1.3 g of tin tetrachloride (4.9 mmol) was added dropwise to the mixture at a room temperature. Subsequently, the mixture was stirred for 18 hours at room temperature. The final product, 3-(trichlorostannyl)propylamine, was employed without isolation in the next process as the toluene solution form.

(5) Synthesis of 3-aminopropyltin tris(methylethoxide)

0.57 g of sodium (0.025 mol) was treated with 80 ml of isopropylalcohol in a 200 ml eggplant type flask and the mixture was heated at 60° C. until sodium was completely dissolved. To this solution 50 ml of an isopropylalcohol solution containing the 3-(trichlorostannyl)propylamine (4.9 mmol), prepared in the aforementioned example (4), was added dropwise at a room temperature. Subsequently, the mixture was stirred while heating for 6 hours at 70° C. The resultant supernatant was separated and concentrated under reduced pressure to yield 2.4 g of the final product of 3-aminopropyltin tris(methylethoxide) (yield=59%).

(1H-NMR spectrum) δ-value 4.20~3.80 (m, 3H, $OCH_3$); 1.94~1.84 (m, 2H, $CH_2N$); 1.38~1.22 (m, 2H, $CH_2$); 1.22 (d, 18H, $CH_3$); 0.94~0.88 (m, 2H, Sn-$CH_2$); 0.34~0.26 (m, 2H, $NH_2$).

EXAMPLE 3

Synthesis of o-[tri(methylethoxide)tin] benzylamine
(1) Synthesis of o-bromobenzylalcohol 4.88 g of o-bromobenzylalcohol was obtained in the same manner as in the synthesis of o-bromo-1-phenylethanol of Example 1-(1), with the use of 4.85 g of o-bromobenzaldehyde (28.9 mmol) instead of o-bromophenon (yield=90.2%).

(2) Synthesis of o-[tri(cyclohexyl)]tin]benzylalcohol 17.2 g of o-[tri(cyclohexyl)]tin]benzylalcohol was obtained in the same manner as in the synthesis of tricyclohexyl[o-(1-hydroxyethyl)phenyl]tin of Example 1-(4), with the exception that 9.40 g of o-bromobenzylalcohol (50.2 mmol), prepared in the aforementioned example (1), instead of o-bromo-1-phenyl ethanol (yield=75.1%).

(3) Synthesis of o-[tri(cyclohexyl)tin]benzylazide 296 mg of o-[tri(cyclohexyl)]tin]benzylazide (0.590 mmol) was obtained in the same manner as in the synthesis of tricyclohexyl[o-(1-azidoethyl)phenyl]tin of Example 1-(5), with the use of 989 mg of o-[tri(cyclohexyl)tin] benzylalcohol (2.04 mmol), prepared in the aforementioned example (2), instead of tricyclohexyl[o-(1-hydroxyethyl) phenyl]tin.

(4) Synthesis of o-[tri(cyclohexyl)tin]benzylamine 453 mg of o-(trichlorotin)benzylamine was obtained in the same manner as in the synthesis of tricyclohexyl [o-(1-aminoethyl)phenyl]tin of Example 1-(6), with the use of 619 mg of o-[tri(cyclohexyl)tin]benzylazide (1.25 mmol), prepared in the aforementioned example (3), instead of tricyclohexyl [o-(1-azidoethyl)phenyl]tin (yield=77.4%).

(5) Synthesis of o-(trichlorotin)benzylamine 200 mg of o-(trichlorotin)benzylamine was obtained in the same manner as in the synthesis of [o-(1-aminoethyl) phenyl]tin trichloride of Example 1-(7), with the use of 439 mg of o-[tri(cyclohexyl)tin]benzylamine (0.956 mmol), prepared in the aforementioned example (4), instead of tricyclohexyl [o-(1-aminoethyl)phenyl]tin.

(6) Synthesis of o-[tri(methylethoxide)tin]benzylamine 198 mg of o-[tri(methylethoxide)tin]benzylamine was obtained in the same manner as in the synthesis of [o-(1-aminoethyl)phenyl]tin (methylethoxide) of Example 1-(8), with the use of 200 mg of o-(trichlorotin)benzylamine (0.881 mmol), prepared in the aforementioned example (5), instead of [o-(1-aminoetbyl)phenyl]tin trichloride (yield=56.0%).

(1H-NMR spectrum)δ-value 0.80~1.70 (m, 21H, $(CH_3)_2CHO$); 3.27~3.44 (m, 2H, $NH_2$); 4.21~4.55 (m, 2H, $CH_2$); 7.22~7.81 (m, 4H, aromatic).

EXAMPLE 4

13.4 g of trimethylol propane (0.10 mol), 86.1 g of methyl acrylate (1.00 mol), and 1.25 g of o-(1-aminoethyl)phenyl] tin tris(methylethoxide) (0.003 mol), obtained as a catalyst in Example 1, were mixed together in a 200 ml three-neck flask, and stirred at room temperature for 30 minutes. The reaction solution was then analyzed, using gas chromatography, to reveal a product yield of 89.4% of trimethylol propane acrylate.

EXAMPLE 5

26.0 g of n-octylalcohol (0.20 mol), 0.86 g of methyl acrylate (0.10 mol), and 0.70 g of o-(1-aminoethyl)phenyltin tris(methylethoxide) (0.004 mol), obtained as a catalyst in Example 2, were mixed together in a 100 ml three-neck flask, and stirred at room temperature for 30 minutes. The reaction solution was then analyzed, using gas chromatography, to reveal a product yield of 75.0% of n-octyl acrylate.

EXAMPLE 6

26.0 g of n-octylalcohol (0.20 mol), 11.6 g of methyl capronate (0.1 mol), and 1.22 g of 3-aminopropyltin tris (methylethoxide) (0.004 mol), obtained as a catalyst in Example 2, were mixed together in a 100 ml three-neck flask, and stirred at room temperature for 30 minutes. The reaction solution was then analyzed, using gas chromatography, to reveal a product yield of 97.0% of octyl capronate.

EXAMPLE 7

10.4 g of L-methyl lactate (0.10 mol), 108.0 g of benzylalcohol (1.00 mol), and 0.21 g of o-(1-aminoethyl)phenyltin tris(methylethoxide) (0.0005 mol), obtained as a catalyst in Example 1, were mixed together in a 100 ml three-neck flask, and stirred at room temperature for 30 minutes. The reaction solution was analyzed, using gas chromatography, to reveal a product yield of 78% of L-benzyl lactate with a 99% optical purity.

EXAMPLE 8

An isopropanol solution (0.053 mmol/g) containing 201 mg of o-triisopropoxytin benzylamine, obtained in Example 3, was introduced under an argon atmosphere into a 20 ml Schlenk flask equipped with a stirrer bar, which had been dried with deairing and kept under atmosphere of argon before used. The solution was then dried under a vacuum to remove the isopropanol.

Subsequently, 228 mg of Methyl 1-(S)-(–)sec-phenethyl-L-2-azetidinecarboxylate and 2.09 g of benzylalcohol were introduced into the Schlenk flask, and stirred at room temperature for 18 hours.

The reaction mixture was subjected to a column chromatography on silica gel, to obtain 255 mg of Benzyl 1-(S)-(–)sec-phenethyl-L-2-azetidine carboxylate (yield=83%).

EXAMPLE 9

320 mg of Diethyl 1,3-dibenzyl-2-oxoimidazolidin-4,5-dicarboxylate was obtained in the same manner as in Example 8, with the use of 398 mg of Dimethyl 1,3-dibenzyl-2-oxoimidazolidin-4,5-dicarboxylate, and 1.78 g of ethanol, instead of Methyl 1-(S)-(–)-sec-phenethyl-L-2-acetidine carboxylate, and benzylalcohol (yield=75%).

EXAMPLE 10

(1) Preparation of 3-tri(butylthio)stannyl propanamine $(BuS)_3SnCH_2CH_2CH_2NH_2$ 20% Isopropanol solution of $(i-PrO)_3SnCH_2CH_2CH_2NH_2$ was treated with excess amount of BuSH (30 mol excess) at room temperature for 2h followed by concentration under vacuum to afford 3-tri(butylthio)stannyl propanamine $(BuS)_3SnCH_2CH_2CH_2NH_2$.

(2) Transesterification of 1-hexanol and methyl acrylate using $(BuS)_3SnCH_2CH_2CH_2NH_2$ In round-bottom flask 1-hexanol (5 mol, 510 g) and methyl acrylate (1 mol, 86 g) were placed and this mixture was stirred at room temperature. Then 4.44 g (0.01 mol, 1 mol %) of $(BuS)_3SnCH_2CH_2CH_2NH_2$, prepared from $(i-PrO)_3SnCH_2CH_2CH_2NH_2$ and BuSH as described above, was added and transesterification was carried out at room temperature for 3 h. The reaction mixture was analyzed by GC using hexylbenzene as a internal standard, which revealed that the described product, hexyl acrylate, was obtained in 50% GC yield.

Comparative Example 1

The same reaction as in Example 4 was performed with the exception that 0.75 g of dibutyltin oxide (0.003 mol) was used as a catalyst. The reaction solution was analyzed, using gas chromatography, to reveal a 0% conversion of the hydroxyl group in the trimethylol propane employed therein.

Comparative Example 2

The same reaction as in Example 4 was performed with the exception that 0.29 g of sulfuric acid (0.003 mol) was used as a catalyst. The reaction solution was analyzed, using gas chromatography, to reveal a 0% conversion of the hydroxyl group in the trimethylol propane employed therein.

Comparative Example 3

The same reaction as in Example 6 was performed with the exception that 1.00 g of dibutyltin oxide (0.004 mol) was used as a catalyst. The reaction solution was analyzed, using gas chromatography, to reveal a 7% conversion of the hydroxyl group in the trimethylol propane employed therein.

Comparative Example 4

The same reaction as in Example 6 was performed with the exception that 0.39 g of sulfuric acid (0.004 mol) was used as a catalyst. The reaction solution was analyzed, using gas chromatography, to reveal a 0% conversion of the hydroxyl group in the trimethylol propane employed therein.

According to the present invention, our organotin compound can catalyze transesterification reaction even under less restrictive reaction conditions, e.g., room temperature, to provide a final product in a high yield and purity wherein optical purity is not affected. Hence, the organotin compound according to the present invention is very useful as a catalyst for transesterification.

What is claimed is:

1. Catalyst for transesterification comprising an organotin compound expressed by the following general formula (I):

(I)

wherein, X, Y, and Z represent independently an alkoxyl group, alkylthio group, halogen atom, or alkyl group; where at least two groups among X, Y, and Z represent an alkoxyl group, alkylthio group, or halogen atom; R represents an alkylene chain; and R' represents a hydrogen atom, or alkyl group, and wherein consecutive carbon atoms of said alkylene chain form a part of an aromatic ring.

2. Catalyst for transesterification comprising said organotin compound according to claim 1, wherein at least one group among X, Y, and Z represents an alkoxyl group.

3. Catalyst for transesterification comprising said organotin compound according to claim 2, wherein X, Y, and Z each represents an alkoxyl group.

4. Catalyst for transesterification comprising said organotin compound according to claim 1, wherein at least one group among X, Y, and Z represents a halogen atom.

5. Catalyst for transesterification comprising said organotin compound according to claim 1, wherein at least one group among X, Y, and Z represents an alkylthio group.

6. Catalyst for transesterification comprising said organotin compound according to claim 2, wherein one group among X, Y, and Z represents an alkyl group.

7. Organotin compound expressed by the following general formula (II):

(II)

wherein, X, Y, and Z represent independently an alkoxyl group, alkylthio group, halogen atom, or alkyl group; where at least two groups among X, Y, and Z represent an alkoxyl group, alkythio group, or halogen atom; R represents an alkylene chain; and R' represents a hydrogen atom or alkyl group, and wherein consecutive carbon atoms of said alkylene chain form a part of an aromatic ring.

8. Organotin compound according to claim 7, wherein at least one group among X, Y, and Z represents an alkoxyl group.

9. Organotin compound according to claim 8, wherein X, Y, and Z each respectively represents an alkoxyl group.

10. Organotin compound according to claim 7, wherein at least one group among X, Y, and Z represents a halogen atom.

11. Organotin compound according to claim 7, wherein at least one group among X, Y, and Z represents an alkylthio group.

12. Organotin compound according to claim 8, wherein one group among X, Y, and Z represents an alkyl group.

13. Organotin compound according to claim 7, wherein R represents an alkylene chain having 3 or 4 carbon atoms.

14. Catalyst for transesterification comprising an organotin compound expressed by the following general formula (I):

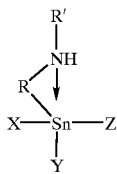
(I)

wherein, X, Y, and Z represent independently an alkoxyl group, alkythio group, halogen atom, or alkyl group; where at least two groups among X, Y, and Z represent an alkoxyl group, alkythio group, or halogen atom; R represents an organic chain; and R' represents a hydrogen atom or alkyl group, and wherein at least one group among X, Y, and Z represents an alkylthio group.

15. Catalyst for transesterification comprising an organotin compound expressed by the following general formula (I):

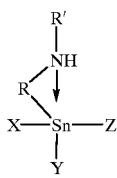
(I)

wherein, X, Y, and Z represent independently an alkoxyl group, alkylthio group, halogen atom, or alkyl group; where at least two groups among X, Y, and Z represent an alkoxyl group, alkylthio group, or halogen atom; R represents an organic chain; and R' represents a hydrogen atom or alkyl group, and wherein one group among X, Y, and Z represents an alkyl group, and at least one group among X, Y, and Z represents an alkoxyl group.

16. Organotin compound expressed by the following general formula (II):

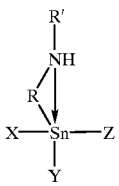
(II)

wherein, X, Y, and Z represent independantly an alkoxyl group, alkythio group, halogen atom, or alkyl group; where at least two groups among X, Y, and Z represent an alkoxyl group, alkythio group, or halogen atom; R represents an alkylene chain; and R' represents a hydrogen atom or alkyl group, and wherein at least one group among X, Y, and Z represents an alkylthio group.

17. Organotin compound expressed by the following general formula (II):

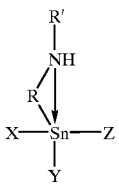
(II)

wherein X, Y an alkoxyl group, alkylthio group, halogen atom, or alkyl group; where at least two groups among X, Y, and Z represent an alkoxyl group, alkylthio group, or halogen atom; R represents an alkylene chain; and R' represents a hydrogen atom or alkyl group, and wherein one group among X, Y and Z represents an alkyl group, and at least one group among X, Y, and Z represents an alkoxyl group.

* * * * *

UNITED STATES PATENT AND TRADEMARK OFFICE
CERTIFICATE OF CORRECTION

PATENT NO. : 6,022,822
DATED : February 8, 2000
INVENTOR(S) : Ryoji NOYORI

It is certified that error appears in the above-identified patent and that said Letters Patent is hereby corrected as shown below:

On the title page item [73], change the name of the third assignee "Sumitomo Company, Ltd." to be --Sumitomo Chemical Company, Ltd.--.

Signed and Sealed this

Thirtieth Day of January, 2001

Attest:

Q. TODD DICKINSON

*Attesting Officer*　　　　　*Director of Patents and Trademarks*